United States Patent
Reaux (10) Patent No.: US 8,371,448 B1
(45) Date of Patent: Feb. 12, 2013

(54) STORAGE SYSTEM FOR MEDICAL WASTE MATERIALS

(75) Inventor: Brian K. Reaux, Red Oak, TX (US)

(73) Assignee: Brian K. Reaux, Red Oak, TX (US)

( * ) Notice: Subject to any disclaimer, the term of this patent is extended or adjusted under 35 U.S.C. 154(b) by 11 days.

(21) Appl. No.: 12/894,449

(22) Filed: Sep. 30, 2010

Related U.S. Application Data (60) Provisional application No. 61/277,964, filed on Oct. 1, 2009, provisional application No. 61/278,055, filed on Oct. 2, 2009, provisional application No. 61/278,370, filed on Oct. 6, 2009, provisional application No. 61/283,171, filed on Nov. 30, 2009, (Continued)

(51) Int. Cl.
*A61B 19/02* (2006.01)
*A61B 19/00* (2006.01)
*B65D 33/08* (2006.01)
*B65D 33/00* (2006.01)

(52) U.S. Cl. ......... 206/570; 206/362; 206/370; 206/438

(58) Field of Classification Search .................. 206/570, 206/370, 554, 363, 372, 373, 362; 383/37, 383/38
See application file for complete search history.

(56) References Cited

U.S. PATENT DOCUMENTS

| | | | | |
|---|---|---|---|---|
| 3,749,237 A | * | 7/1973 | Dorton | 206/438 |
| 4,234,086 A | * | 11/1980 | Dorton | 206/362 |
| 4,295,537 A | * | 10/1981 | McAvinn et al. | 177/15 |
| 4,415,089 A | * | 11/1983 | Ruffa | 211/85.13 |
| 4,422,548 A | * | 12/1983 | Cheesman et al. | 206/370 |
| 4,713,136 A | * | 12/1987 | Li | 156/229 |
| 4,832,198 A | * | 5/1989 | Alikhan | 206/438 |
| 4,844,259 A | * | 7/1989 | Glowczewskie et al. | 206/370 |
| 4,887,715 A | * | 12/1989 | Spahn et al. | 206/370 |
| 4,953,765 A | * | 9/1990 | Little et al. | 224/583 |
| 5,048,683 A | * | 9/1991 | Westlake | 206/362 |
| 5,100,000 A | * | 3/1992 | Huseman | 206/554 |
| 5,170,804 A | * | 12/1992 | Glassman | 128/849 |
| 5,429,234 A | * | 7/1995 | Bohannon | 206/362 |
| 5,871,015 A | | 2/1999 | Lofgren et al. | |
| 6,607,170 B1 | * | 8/2003 | Hoftman | 248/129 |
| 6,827,212 B2 | | 12/2004 | Reaux | |
| 7,040,484 B1 | * | 5/2006 | Homra et al. | 206/363 |

(Continued)

OTHER PUBLICATIONS

Webpages from https://www.aorn.org/news/february2010news/counts; accessed Mar. 19, 2010; pp. 1-5.

(Continued)

*Primary Examiner* — Steven A. Reynolds (57) ABSTRACT

A storage system for storing used surgical towels, sponges or other medical waste materials includes a rear panel having an upper portion and a lower portion formed from a flexible sheet material. The upper portion of the rear panel has a coupling mechanism for coupling the device to a sterile structure of a surgical room. In certain embodiments, the rear panel may have a weakened partition area for separating the lower portion from the upper portion. A compartment assembly is formed by two or more flexible compartments provided on the lower portion of the rear panel. Each compartment may be liquid impervious and have an upper opening for introducing materials into the compartment. Each compartment has a forward wall that is at least partially transparent so that the contents of the compartment are observable. All components of the storage device may be sterile for use in a sterile environment. In certain embodiments, a storage system may be provided by coupling at least two storage devices together.

16 Claims, 6 Drawing Sheets

Related U.S. Application Data provisional application No. 61/283,909, filed on Dec. 10, 2009, provisional application No. 61/335,008, filed on Dec. 30, 2009, provisional application No. 61/335,894, filed on Jan. 12, 2010, provisional application No. 61/339,151, filed on Mar. 1, 2010, provisional application No. 61/340,729, filed on Mar. 20, 2010, provisional application No. 61/395,415, filed on May 13, 2010, provisional application No. 61/397,262, filed on Jun. 9, 2010, provisional application No. 61/398,257, filed on Jun. 23, 2010.

(56) References Cited

U.S. PATENT DOCUMENTS

| | | | | |
|---|---|---|---|---|
| 7,104,201 | B2* | 9/2006 | Comeaux et al. | 108/90 |
| 7,540,039 | B2 | 6/2009 | Reaux | |
| 7,806,594 | B2* | 10/2010 | Trinko | 383/37 |
| 2003/0085246 | A1* | 5/2003 | Reisman et al. | 224/275 |

OTHER PUBLICATIONS

Webpages from http://www.nothingleftbehind.org/; accessed Sep. 30, 2010; pp. 1-2.

Presentation slides from presentation at Dallas VA Hospital, Dallas, Texas; Mar. 2010; pp. 1-3.

Webpages from http://www.nothingleftbehind.org/Retained_Surgical_Sponges.html; accessed Mar. 19, 2010; pp. 1-4.

Elkay Plastics Co. Inc., Healtcare Specialty Plastic Bags product catalog; pp. 1-34.

* cited by examiner

STORAGE SYSTEM FOR MEDICAL WASTE MATERIALS

CROSS-REFERENCE TO RELATED APPLICATIONS

This application claims the benefit of U.S. Provisional Application Nos. 61/277,964, filed Oct. 1, 2009; 61/278,055, filed Oct. 2, 2009; 61/278,370, filed Oct. 6, 2009; 61/283,171, filed Nov. 30, 2009; 61/283,909, filed Dec. 10, 2009; 61/335,008, filed Dec. 30, 2009; 61/335,894, filed Jan. 12, 2010; 61/339,151, filed Mar. 1, 2010; 61/340,729, filed Mar. 20, 2010; 61/395,415, filed May 13, 2010; 61/397,262, filed Jun. 9, 2010; and 61/398,257, filed Jun. 23, 2010, each of which is incorporated herein by reference in its entirety for all purposes.

BACKGROUND

In surgical procedures, used sponges and towels that are used to soak up blood and other fluids during the procedures are disposed of by placing them in a kick bucket that is typically placed on the floor adjacent to the operating table. Not infrequently, the sponges will miss the bucket and drop to the floor or other area creating an unsanitary and potentially unsafe environment.

It is typical practice during or after the procedure to account for all of the sponges to ensure that no sponge has been left inside the patient after the surgical procedure. Thus, the used sponges in the kick bucket may be periodically transferred to a sponge counter unit that is typically suspended on an IV pole to facilitate counting of the used sponges. Transfer of the sponges from the bucket to the sponge counter unit requires the surgery room personnel to bend down to access the bucket, which is undesirable. The bucket is also located in a non-sterile environment so that the surgery room personnel may have to rescrub. Movement of the bucket may also be required to facilitate transfer of the sponges to the counting unit.

The present invention eliminates the need for a kick bucket and also allows surgery room personnel to dispose of used sponges while maintaining sterility and providing an effective means for accounting for the used sponges, as well as provide other advantages.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

Figures 1, 2:
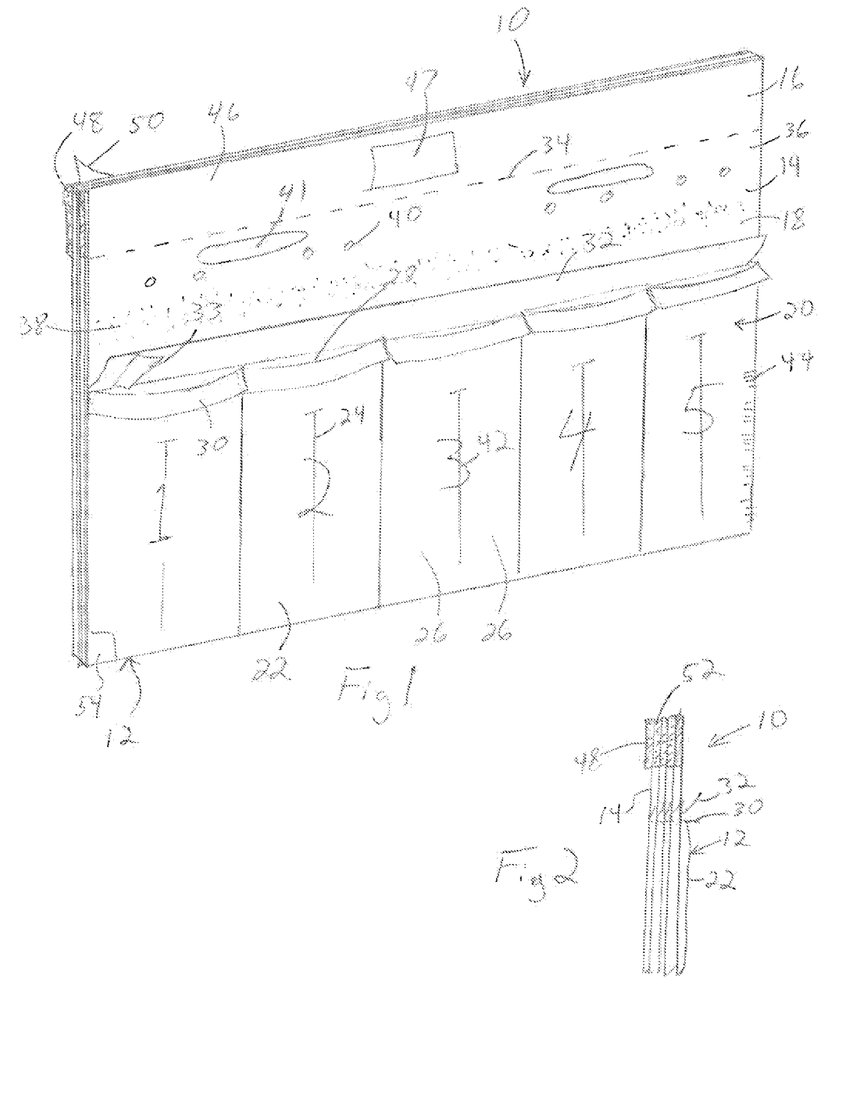
FIG. 1 is a front perspective view of a storage system for surgical sponges, towels and other medical waste materials.
FIG. 2 is side elevational view of the system of FIG. 1.

Referring to FIG. 1, a storage system or assembly 10 for storing surgical towels, sponges and other medical waste materials is shown. The storage system 10 may include a stack of individual storage devices 12 that are coupled together. In other embodiments the storage system may include only a single device 12. Each storage device 12 includes a rear panel 14 that is formed from a layer of sheet material, which may be rigid or flexible sheet material. The rear panel 14 has an upper portion 16 and a lower portion 18.

Each storage device 12 includes a compartment assembly 20 that is provided on the lower portion 18 of the rear panel and is formed by flexible pouches or compartments 22. Any number of compartments 22 may be provided on each device 12. In certain embodiments, two or more compartments are provided. In other embodiments, 5 or 10 compartments may be provided on each device 12 or provided in multiples of 5 (e.g. 5, 10, 15, 20, etc.). The compartments 22 may be arranged in a side-by-side configuration and oriented in rows that extend across the width of the device 12. For example, 5 or 10 compartments may be arranged in a horizontal row. More than one row of compartments 22 may also be provided on each device 12. The compartments 22 may also be arranged in one or more vertical columns.

It should be noted in the description, if a numerical value or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or refer to, it is to be understood that the inventor appreciates and understands that any and all points within the range are to be considered to have been specified, and that inventor possesses the entire range and all points within the range.

The compartments 22 are formed from a flexible sheet material that may be the same or different material from that forming the rear panel 14. In certain embodiments, the compartments 22 of the compartment assembly 20 may be formed from a single sheet of material that forms a forward wall of the compartment that is welded, laminated, glued, taped or otherwise coupled to the rear panel 14 along the side edges of the compartments 22 to form the individual compartments 22, with the rearward wall of the compartment being formed from the rear panel 14. In other embodiments, the compartments 22 may include a separate forward and rearward wall that are joined together along the side edges of the compartments and then coupled to the rear panel 14. The forward wall of the compartment 22 may be at least partially or completely transparent to allow the contents of the compartment 22 to be observed through the forward wall. A portion of the material forming the rear panel 14 may also be folded upward at the bottom to provide the sheet material forming the compartments 22. In other embodiments, individual sheets may be used to form one or more of the compartments 22. The compartments 22 provided on the device 12 are typically liquid impervious to contain any liquids (e.g. blood) from the sponges, etc.

The compartments 22 are sized and configured to hold used sponges, towels, etc. used in the surgical procedure. As a non-limiting example, each compartment 22 may have a width of from about 2 to about 10 inches or more, more typically from about 3 to about 6 inches, and a height of from about 2 to about 10 inches or more, more typically from about 2 to about 6 inches. The sizes of compartments in each row or column may be the same or different.

In certain embodiments, one or more or all of the compartments 22 may have a releasable divider 24 that divides each compartment into two or more sub-compartments 26. The releasable divider 24 may be provided by a soft weld, a low tack adhesive or other releasable fastening mechanism (e.g. snap, button, hook and loop, etc.) that releasably couples the sheet material of the compartments 22 and/or to the material of the rear panel 14 and can be selectively released so that sub-compartments may be eliminated. The sub-compartments 26 of each compartment 22 may be the same or different sizes. The releasable divider 24 may be provided along all or a portion or portions of the length of the compartment 22 or may merely be a single point or multiple points, such as provided by a spot weld or snap fastener.

Each compartment 22 has an opening at the upper end to facilitate insertion and introduction of materials into the interior of the compartment 22. A pull tab or lip 30 may be provided at the upper end of the forward wall of each compartment 22 to facilitate opening of the compartment 22. The pull tab 30 may be a continuous strip that extends across the width of the row of compartments or may be multiple strips (as shown) that are each used with an individual compartment. The pull tab 30 may be provided by an extended piece of the sheet material forming the forward wall of each compartment or may be separate member that is coupled to the sheet material of the compartment 22.

A compartment closure 32 may also be provided with the compartments 22. In the embodiment shown in FIG. 1, the closure 32 is formed by a separate member that is coupled to the rear panel 14, and may be provided with a layer of adhesive, such as pressure sensitive adhesive (PSA), with a release liner 33 that can be selectively removed to expose the adhesive. In other embodiments, the closure may be formed by all or a portion of the pull tab or lip 30, which may also be provided with adhesive and a release liner. The closure 32 may be folded down to close or seal the compartments 22, whereas the tab or lip 30 or other closure member may be folded up to close or seal the compartments 22. The adhesive of the closure 30 or 32 may be releasable so that the compartment 22 may be closed and reopened. The adhesive may also be releasable and reusable so that once it is released it may be reapplied for reclosing or repositioning. In other embodiments, the closure may be a permanent closure that cannot be reopened. Other compartment closures may also be used. The compartment closure may also include an interlocking zip fastener wherein interlocking mating strips of the zip fastener are provided at the upper end of the forward and rearward walls of the compartment 22 and/or on lip 30 or closure 32. Examples of other compartment closures that may also be used may include double-sided tape, hook and loop fasteners, magnets, snaps, buttons, a tab and slot, etc. As used herein, adhesive layers described may be adhesive applied directly to the sheet materials of the device or may be provided by separate layers of material, such as double sided tape, unless expressly stated otherwise or is otherwise apparent from their context.

The rear panel 14 of the storage device 12 may include a weakened partition area 34 for separating the upper portion 16 from the lower portion 18. The weakened partition area 34 is formed from a line of weakness of the material forming the rear panel that facilitates the separation of the upper and lower portions 16, 18 and removal of the compartment assembly 20 from the rest of the device 12. The weakened area 34 may include, for example, a line of perforations, scoring, a line of thinness formed in the material, etc.

In the embodiment shown, a portion 36 of the rear panel 14 below the weakened area 34 extends above the openings 28 of the row of compartments 22. In certain embodiments, this portion 36 forms a flap that may also be used to form a closure of the compartments 22, with the closure 32 being optionally eliminated. A layer of adhesive 38, which may be provided with a release liner strip (not shown), may facilitate closing of the compartments. The portion 36 may also be provided with other closure mechanisms or cooperating components, such as the zip fastener, double-sided tape, hook and loop fasteners, magnets, snaps, buttons, a tab and slot, etc., as discussed previously.

The materials forming the rear panel and compartment assembly are typically polymer or plastic materials, although other materials may be used. The materials may be sterilizable so that they do not degrade under certain sterilization techniques. The sheet materials forming the device may be flexible but have sufficient rigidity such that the device 12 or system 10 will not fold onto itself. The polymeric sheet material forming the components of the device 12 may have a thickness of from about 1 to about 10 mils, with from about 1.5 to 5 mils being more typical, and from to 2 to 3 mils being more typical. In certain embodiments, all or a portion of the rear panel 14 or other components of the device 12 may be clear, opaque or non-transparent. In some embodiments, the rear panel 14 may be a different color (e.g. red, black, white, blue, green, pink, yellow, orange, purple, etc.) or combination of colors that is different from the material forming the forward wall of the compartments 22. In certain embodiments, where multiple devices are coupled together as a system 10, the rear panel 14 of the rearmost device 12 may serve as a base and have a greater thickness and be rigid or have a greater rigidity than the rear panels 14 of the remaining devices 12, which may be flexible. Additionally, the rear panel 14 of the rearmost device 12 may be formed from a different material, such as paperboard, cardboard, rigid plastic, metal, wood, particle board, fiberglass, composite materials, etc.

Provided below the weakened area 34 and formed in the material of the rear panel 14, such as on extended portion 36, or otherwise provided on the compartment assembly 20, may be one or more holes 40. The holes 40 may be configured, sized and arranged for engagement with hooks, rods or other members, such as provided on IV poles, or other structures, for hanging the compartment assembly 20 for counting after the compartments 22 have been filled. The holes 40 may be surrounded by an additional reinforcing material, such as a layer of polymeric material, paperboard, etc., applied to the rear panel material to prevent tearing of or damage to the holes 40 during use.

Hand carry openings 41 may also be provided the lower portion 18 to facilitate carrying the compartment assembly 20, device 12 or system 10.

Areas of the device 12 may be provided with various indicia that is printed or formed on or into the materials forming the device 12. This may include compartment numbers 42 designating the number of each compartment. Measurement indicia or markings 44 (e.g., inches, ml or cc) may also be provided on or along one or more of the compartments 22 to indicate a height or volume of liquid (e.g. blood) that may be contained within the compartment 22. Indicia indicating entry fields, such as a block or blank line, for entering information onto the device 12 or portions thereof with a marker or other device may be provided on the device. The indicating indicia for the entry fields may include prompts such as "patient name," "date," "total count," etc. The prompting indicia may include prompts for patient information, surgery room designation, date information, sponge count information, etc. Biohazard indicia may also be provided on the device indicating that the device 12 or compartment assembly 20 may be a biohazard once it has been used. Trademark and product identifying indicia may also be provided. At least some indicia may be provided on the upper portion 16 of the rear panel 14. At least a portion of the upper portion 16 may constitute a header 46, which may be formed as a strip along the uppermost position of the upper portion 16 above the partition 34 and provides a surface where indicia may be provided.

A clear slot or window 47 may also be provided on the device 12 or system 10 for insertion of a card or device, which may contain patient or other information.

As discussed previously, the storage device 12 may be used alone or provided as a system or assembly wherein multiple storage devices 12 are coupled together. The upper portion 16 of the rear panel 14 on the rearmost device 12 (if multiple storage devices are used) or on the single device 12 (if used alone) is provided with a coupling mechanism for coupling to structures in the surgery room or other areas. As shown in FIG. 2, the coupling mechanism may be in the form of a layer of adhesive 48 that is provided on the rearward surface of the upper portion 16 of the rear panel 14, such as along the header portion 46. The adhesive 48 may be a continuous or non-continuous layer and may extend along the entire width or only portions of the width of the device 12. The adhesive maybe a PSA adhesive or other adhesive and may be releasable or permanent. The adhesive 48 may also be releasable and reusable. The adhesive 48 should have sufficient strength to hold the device 12 or system 10 in place when applied to a structure even after all the compartments 20 of the front compartment assembly 20 being used are filled with materials. A removable release liner 50 that may be selectively removed may initially cover the adhesive 48 prior to use. In certain embodiments employing the system 10 where multiple devices are coupled together, the entire or substantially the entire rearward surface of the rearmost panel 14 may be provided with an adhesive. Examples of other suitable coupling mechanisms, which may be used on a single device or a multiple device system, include adhesive, hook and loop fasteners, holes, sleeves or apertures, which may be reinforced and formed in the rear panel 14, snaps, buttons, clips, hooks, clasps, magnets, double sided tape, sleeve for receiving a support rod, etc., and combinations of these. In systems 10 where the upper portions 16 of the rear panels 14 are permanently coupled together, the coupling mechanism may be provided with any or all the coupled upper portions of the devices 12 as a whole and not merely to the rearmost device 12.

Referring to FIGS. 1 and 2, the system 10 is shown as a stack of multiple devices 12 that are coupled together at the upper portions 16 of the rear panel 14. From 2 to 50 or more devices may be coupled together. The devices 12 are shown laminated together with a layer of adhesive 52 (FIG. 2) between each layer of the upper portion 16 of the rear panels 14, such as along the header area 46. The area below the upper portion 16 or header 46 may be free of adhesive to facilitate removal of the lower portion 18.

In certain embodiments, the adhesive 52 is a releasable adhesive. In such embodiments, the partition area 34 may be eliminated and removal of each device 12 may be facilitated by removing the entire device 12 from the remaining devices 12 of the system 10. In such cases, the releasable layer of adhesive 52 should still have sufficient strength to hold the device 12 in place when the compartments 22 of the forward device 12 is filled. Additionally, the devices 12 may be removed one at a time and used in an individual manner, with the adhesive strip 52 being retained on the back of the rear panel 14 so that it may be applied to a structure for use. Other releasable coupling means may also be used so that the individual devices 12 may be removed from the stack of devices and used in an individual manner.

For those systems employing the weakened partition area 34 wherein the lower portion may be removed, the upper portions 16 may be permanently coupled together. This may include the use of rivets, staples, heat welding, nails, glue, permanent adhesive, etc.

Figure 8:
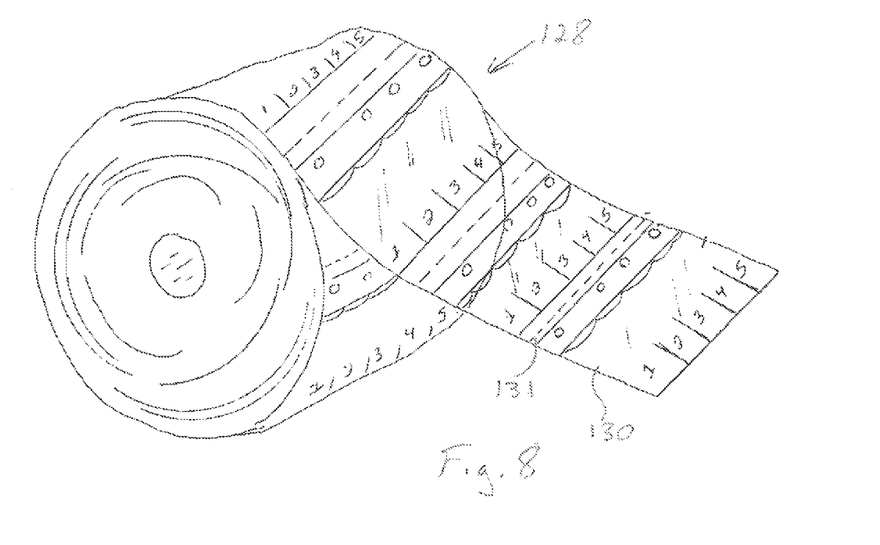
FIG. 8 is a perspective view of storage assemblies or devices supplied in a roll.

In forming the storage system or assembly 10, the various layers of sheet material(s) forming each device may be fed as continuous or non-continuous sheets, include in the polymeric materials, adhesive, release liners, etc. They may be fed from rolls. These may be fed to a laminator or other system or systems were the materials are laminated together, sealed, welded, scored and/or perforated, punched, die cut and folded or configured into a size and/or shape for packaging, if desired. The devices 12 or systems 10 may be packaged in a container or other packaging for distribution and use. In certain embodiments, the devices 12 or systems 10 may be provided in continuous rolls, such as shown in FIG. 8.

Additionally, the devices 12 or systems 10 may be sterilized. Sterilization may occur prior to or after packaging of the devices or systems in any container. Sterilization methods may include sterilizing with gamma ray or other radiation, ethylene oxide (EO) or other sterilizing gas, steam or other suitable sterilization methods that do not significantly degrade the product.

In certain embodiments, an RFID device 54 may be supplied with the device 12 or system 10.

In use, the individual device or system is taken out of any packaging. The device or system may be sterile and sterile handling techniques may be employed when handling the device or system. The device or system is then coupled with the coupling mechanism 48 to a medical drape, such as a table drape or patient drape, mayo stand cover, surgical fabric covering, or directly to a surgical table, such as a back table or back work table. The structure to which the device or system is coupled to may have any cooperating coupling mechanism that is necessary to facilitate coupling, such as hook and loop fastener, steel or magnet material, frame, snap, etc. In many instances, the device or system will be coupled to the surface of a drape or mayo cover. In the embodiment shown, the release liner 50 is removed from the adhesive 48 and it is applied to the surface of the selected structure.

In certain applications, the device 12 or system 10 is used in a sterile manner. To facilitate this, the device 12 or system 10 is applied to the medical drape, mayo stand drape, etc. so that the openings 28 of the compartments 22 are at or above the sterile zone of the surgical area. In this way, the surgery personnel may remove used sponges, towels or other materials from the sterile surgery environment and simply place them into the compartments 22 or sub-compartments 26, which are also within the sterile zone. The compartments 22 may then be closed using the closure (e.g. 30, 32), if desired, and the compartment assembly 20, such as by partitioning at the partition area 34, or the entire device 12 may be removed, and taken to a counting area, where the assembly 10 or device 12 may be hung on hooks or other structures for counting by use of the holes 40 or other means. The personnel removing the used sponges or towels in this way may not compromise sterility, which was not the case with use of the prior art kick bucket.

Figure 3:
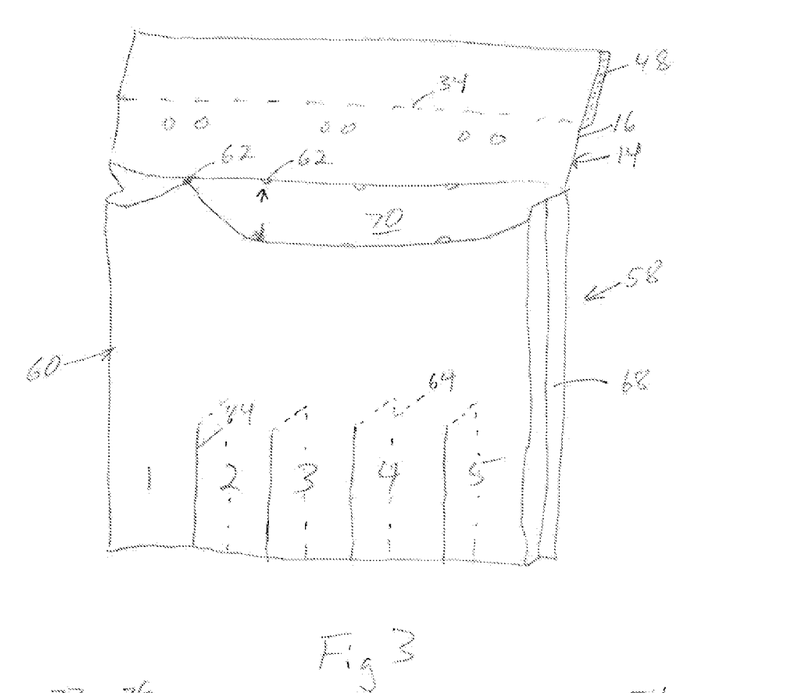
FIG. 3 is a front perspective view of another embodiment of a storage system for surgical sponges, towels and other medical waste materials.

Other variations of the device or system may also be provided. FIG. 3 shows another variation of a storage device 58 that may be used individually or as a system with multiple devices. The device 58 is similar to the device 12 with similar components labeled with the same reference numerals. The device 58 includes a compartment assembly 60 wherein individual compartments are formed by means of releasable spaced apart dividers 62, which may be in the form of soft welds or other releasable fastening mechanisms, located at the upper end of the front wall. The dividers 62 join the front wall of the compartment assembly 60 to the rear panel 14. In certain embodiments, non-releasable dividers 64 may be provided in the lower portion of the compartment assembly 60. The sides 68 and dividers 64 of the compartment assembly 20 are also shown as being gusseted and formed from additional sections of material that allow the expansion of the compartments.

The device 58 can be used where each of the individual compartments stay intact by retaining the releasable dividers 62. In the embodiment shown, the releasable dividers 62 are parted to define a single large compartment 70. In certain applications, all of the dividers may be releasable. In the present embodiment, the dividers 64 remain intact. These may be used to store used sponges or other materials, with the large compartment 70 being used to store other materials, such as trash, above the smaller compartments 72, which may be used for individual sponges.

Figure 4:
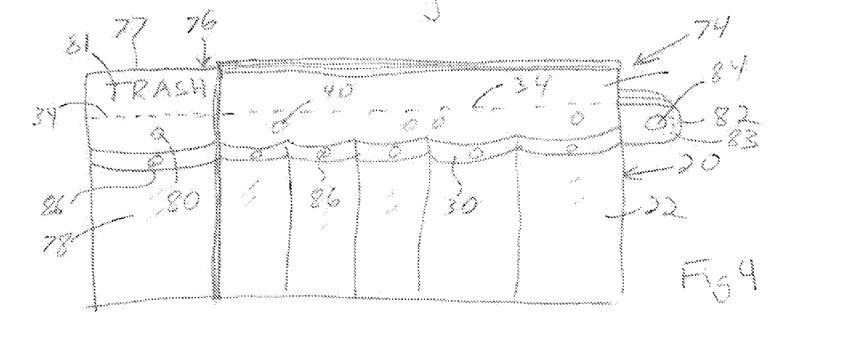
FIG. 4 is a front view of still another embodiment of a storage system for surgical sponges, towels and other medical waste materials that includes a trash storage area.

FIG. 4 shows another embodiment of a system 74 that includes one or more devices 76. The system 74 and device 76 are also similar to the system 10 and device 12, with similar components labeled with the same reference numerals. At least one of the devices 76 is supplied with one or more extended portions 77 that forms a trash compartment 78 that may be formed from the same materials as the compartments 22 and configured similarly with similar components. The trash compartment 78, however, may be larger than the other compartments 22 to facilitate holding of trash or other materials and may also be provided with its own hang hole 80. Indicia 81 may be provided to indicate its use as a trash compartment. The partition area 34 may also be provided for removal of the trash compartment.

The device 76 of the system 74 are also shown as including a pull tab 82 along the side edge of the device. The pull tab 82 may be configured as a ring and be provided with an aperture 84 that facilitates removal of the device 12 or the compartment assembly 20, which may include the trash compartment 78. The tab 82 may also be texturized 83 to facilitate grasping of the tab 82. Additionally, the pull tabs or lip 30 may also be provided with apertures 86 to facilitate grasping of the lip 30 to open the compartments 22 or trash compartment 78.

Figure 5:
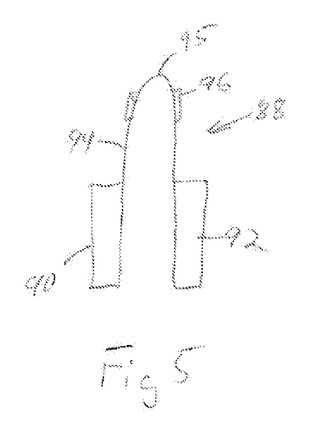
FIG. 5 is a side elevational view of a storage system with oppositely faced compartment assemblies provided on a folded rear panel.
Figure 6:
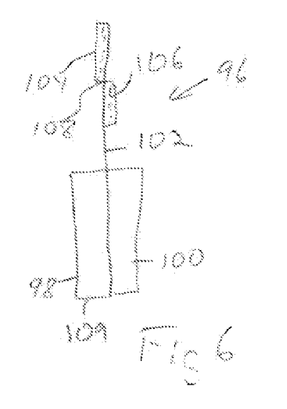
FIG. 6 is a side elevational view of a storage system with oppositely faced compartment assemblies provided on opposite sides of a rear panel.

FIGS. 5-6 show various embodiments of systems that employ oppositely disposed compartment assemblies. FIG. 5 shows a system 88 wherein two devices are essentially provided by compartment assemblies 90, 92 that are facing opposite directions and are joined together by a common rear panel 94. The panel 94 is folded over at fold 95, with the compartment assemblies 90, 92 being provided on the same surface of the rear panel 94, as is shown. Adhesive or other coupling mechanisms 96, with or without a release liner, may be provided on either side at the area just below the fold 95. The compartment assemblies 90, 92 may each be different or the same. For example, the compartment assembly 90 may be a five compartment assembly and the compartment assembly 92 may be a ten compartment assembly. Either compartment assembly 90, 92 may be used as desired by turning the assembly 88 so that it is facing in the desired direction.

FIG. 6 shows another embodiment of a system 96 wherein two devices are essentially provided by opposite facing compartment assemblies 98, 100 that are joined to opposite surfaces of a common rear panel 102. Adhesive strips 104, 106 may be provided on opposite surfaces of the rear panel 102. The adhesive strips 104, 106 may be vertically aligned at the same level on the opposite surfaces of the rear panel 102. In the embodiment shown, however, the adhesive strips 104, 106 are vertically offset, with one being located above the other. A weakened partition area 108, such as perforations, may be provided between the adhesive strips 104, 106, so that the portion of the rear panel 102 with the upper adhesive strip 104 may be removed, if desired. The compartment assemblies 98, 100 of the system 96 are also shown as being gusseted and provided with flat bottoms 109 so that the system 96 may be stood upright on a support surface when expanded, if desired, without any other support. The compartment assemblies 98, 100 may be the same or different (e.g. 5 compartments and 10 compartments).

Figure 7:
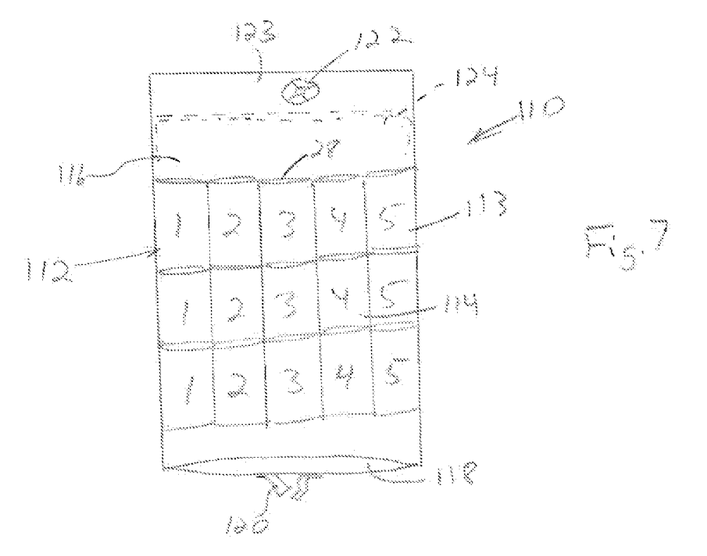
FIG. 7 is a front elevational view of a storage system employing a trash bag.

Referring to FIG. 7, another embodiment of a storage system 110 is shown. The storage system includes a storage device or system 112 that may be similar to those previously described that includes a compartment assembly 113 with various storage compartments 114. In the embodiment shown, the compartments 114 of the assembly 113 are arranged in a row of five marked storage compartments, with three vertically spaced rows of the five compartments 114. The compartments 114 are coupled to a large flexible container or bag 116, which is in the form of a flexible polymeric or plastic trash bag. In certain embodiments, the storage device or system 112 may be a separate device that includes a rear panel (e.g. rear panel 14) that is applied to the surface of the trash bag 116. In other embodiments, the rear panel is formed by a portion of the wall of the trash bag 116 itself. The trash bag 116 serves as the rear panel of the device. More than one compartment assembly 113 may be provided on the trash bag 116, such as opposite sides of the bag 116. The trash bag 116 may be a liquid impervious bag and may be colored or clear. In certain instances, the bag 116 may be colored red or provided with indicia to indicate that it may contain or be used for contaminated waste. Other colors may also be provided that are indicative of its use.

In the embodiment shown, the openings 28 of the compartments 114 are oriented in opposite directions from the lower or open end 118 of the bag 116. In other embodiments they be oriented in the same or a different direction (e.g. perpendicular). The bag 116 may have incorporated at its lower or open end 118 a closure device 120. The closure device 120 is shown as draw string ties that are incorporated into a seam or sleeve located at the open end of the bag 116. Other closure devices may be used as well, including but not limited to, zip fasteners, tape, extended portions of material of the bag that can be tied together, as well as other fastening mechanisms, such as those that have been previously described herein for closure mechanisms.

At the opposite or upper end of the bag 116 is a coupling device 122 for coupling the system 110 to a supporting structure. The coupling device 122 is shown as an aperture formed in the material of the bag 116. The aperture 122 may be reinforced and may be sealed around its perimeter so that the bag 116 remains liquid impervious. In the embodiment shown, a sealed header 123 is provided. Other coupling devices may also be employed for the coupling device 122, adhesive, snaps, buttons, clips, hooks, clasps, magnets, double sided tape, sleeve for receiving a support rod, etc., and combinations of these. In certain embodiments, the coupling device 122 is a plastic, metal or paper board hanger or hook, such as a paper door-knob hook or aperture that is used to hang materials on a door knob.

In certain embodiments, an internal frame 124 may be provided with the system 110 to facilitate spreading of the bag 116 in a flat and/or expanded configuration, as shown. The frame 124 may also be external. The frame 124 may be formed from plastic, paper, metal (e.g. metal wire), etc. In certain embodiments, the coupling device 122 may be incorporated into the frame 124.

In certain embodiments, multiple bags 116, each with at least one compartment assembly 113, may be employed with the system 110. The multiple bags 116 may be coupled together along the upper end, such as at the header 123. The multiple bags 116 may be releasably or permanently coupled together. The coupling may be accomplished by similar methods such as those described for coupling the multiple devices 12 that have been previously described. In certain embodiments, the bags or an extended portion thereof may be laminated together, such as by heat lamination or welding. The thickness of such laminated material may provide sufficient rigidity such that the laminated portion serves as the frame 124. In certain embodiments, the bottom bag 116 may be provided with the coupling device 122, such as a strip of adhesive, with the multiple bags of the system 110 essentially being used liked the system 10, previously described.

As shown in FIG. 7, the upper end of the bag or bags of the system 110 is shown with a weakened partition area 126, such as a line of perforations, scoring, etc. This may allow separation of a bag or bags 116 from the upper portion or header 123, such as when multiple bags 116 are used with the system 110. In other embodiments, multiple bags 116 may be releasably coupled together, such as through the use of a releasable adhesive provided at the upper ends of the bags 116.

The system 110 may be sterile or non-sterile.

In use, the system 110 is hung on a support structure, which may be in a sterile or non-sterile environment, such as through the use of the coupling device 122 and the compartments 114 of the compartment assembly 113 are used to store and count sponges and the like. After the sponges are stored and counted, the bag 116 may be parted at the partition 126 if one is provided or otherwise released from any multiple bags. The bag 116 may then be inverted and turned inside out so that the compartment assembly or assemblies 113 or contained within the interior of the inverted bag 116. The closure device 120 may then be used to close the bag 116.

Any of the systems or devices previously described may be provided in a roll, such as shown at 128 in FIG. 8. As shown, multiple devices or systems 130, which may be the same as the devices 12, device 58, system 10, system 88, system 110, etc. previously described, are provided in a continuous roll wherein each individual device or system 130 is separated from the roll 130 by a weakened partition area 131. In this way, an individual device or system 130 may be removed one at a time as needed.

Figure 9:
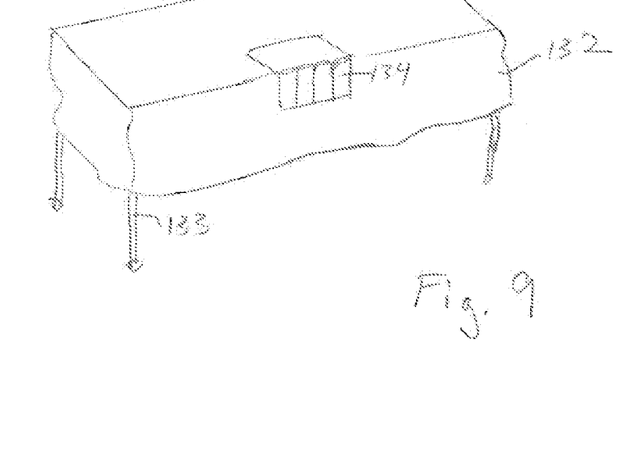
FIG. 9 is a perspective view of a medical drape incorporating a storage system that is positioned on a table.

Referring to FIG. 9, any of the storage devices or systems previously described may be incorporated into a drape, such as the sterile drape 132. The drape 132, which may be paper, plastic or fabric material or a combination of such materials, is shown with a device or system 134 like those previously described. The drape 132 may be a table drape for a table 133, such as a back table or back work table drape, or the drape 132 may be a patient drape. The device or system 134 may be coupled to the drape 132 at a location so that it is properly positioned during use, such as at the table edge, when the drape 132 is unfolded and placed over the table or patient. The position of the device or system 134 may be a sterile position or the openings of the compartments of the device may be at a sterile position, such as at are above the table edge, with the compartments of the device or system 134 hanging along the side in a generally vertical orientation. The device 134 may be permanently or releasably coupled to the drape 132 and may be prepackaged with the drape 132, with the device 134 being folded with the drape 132 and being packaged in a sterile condition. The device 134 may be folded within the drape 132.

Figure 10:
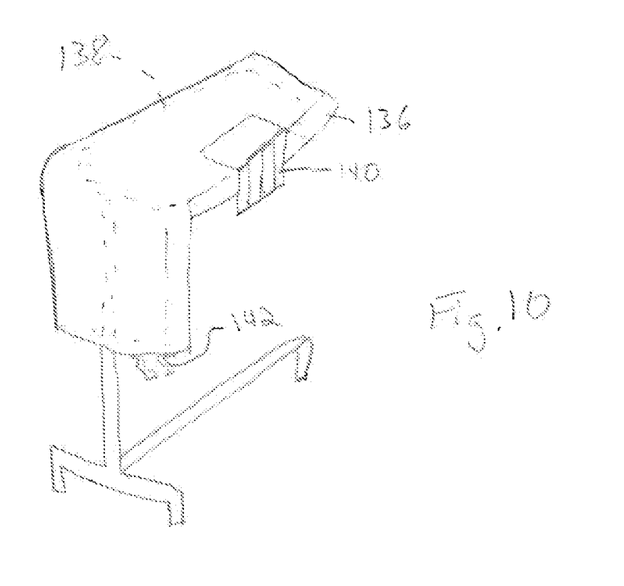
FIG. 10 is a perspective view of a mayo stand cover incorporating a storage system that is positioned on a mayo stand.

Referring to FIG. 10, any of the storage devices or systems previously described may be incorporated into a mayo stand cover 136. The mayo cover 136, which may be paper, plastic or fabric material or a combination of such materials, may be configured as a bag that drapes over and fits over the mayo stand 138. An example of a mayo stand cover is described in U.S. Pat. No. 5,871,015, which is incorporated herein by reference. A device or system 140 like any of those previously described is coupled to the cover 136. The device or system 140 may be coupled to the cover 136 at a location so that it is properly positioned during use, which may include hanging over the edge of the mayo stand 138, so that the compartments of the device or system 140 hang along the side in a generally vertical orientation. During use, the device or system 140 or portions thereof may be at a sterile position. The device 140 may be permanently or releasably coupled to the drape cover 136 and may be prepackaged with the cover with the device 140 being folded with the cover 136 and being packaged in a sterile condition. The device or system 140 may be folded within the cover 136. A closure device 142, which may be a draw string or other device, such as those described for the trash bag 116, may be used to close the open end of the mayo cover 136, which itself may be used as a trash bag or container that may be inverted to contain the used device 140, just as with the bag 116.

Figure 11:
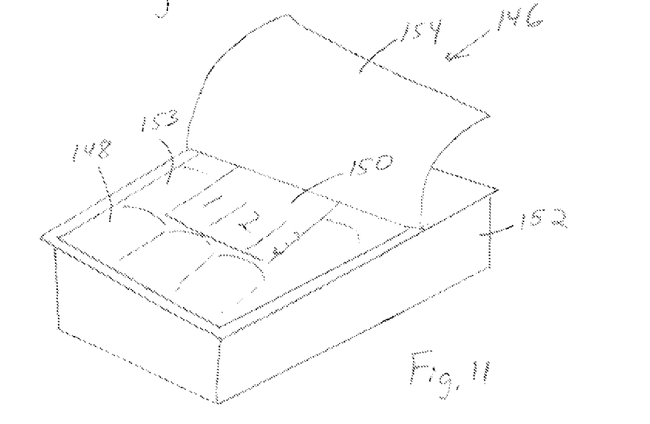
FIG. 11 is a perspective view of a kit containing sponges and a storage system for surgical sponges, towels and other medical waste materials.

Referring to FIG. 11, a kit 146 is shown wherein a prepackaged set of one or more (e.g. 5 or 10 sponges) sterile sponges or towels 148 is provided along with one or more storage devices or systems 150, which may include any of those storage devices or systems described herein. The device(s) 150 may be provided in a folded configuration. In certain embodiments, the number of compartments of the device or devices 150 may corresponding to the number of sponges or towels 150 contained in the kit 146 (e.g. 5 sponges with 5 compartments or 10 sponges with 10 compartments). The sponges or towels 148 and the device 150 may be contained in a rigid or flexible container 152 with the opening 153 of the container 152 being sealed with a removable cover 154. The sponges or towels 148 may include lap sponges, x-ray detectable sponges or towels (e.g. Ray-Tec® sponges), non-x-ray-detectable sponges or towels, etc., which may be all the same or different. In other embodiments, the sponges or towels 148 and device 150 may be sealed entirely within a flexible packaging material (e.g. paper or plastic) to form the kit. The entire kit 146 with its components may be sterilized together or the components of the kit may be sterilized separately using known sterilization techniques. In certain embodiments, the sponges or towels 148 are placed in the bottom of the container 152, with the device or system 150 being placed on top of the sponges or towels 148. In other embodiments, the device or system 150 may be placed in the bottom of the container 152 with the sponges or towels 148 being placed on top of the device 150. In this way, when the container 152 is opened, the contents may be dumped out on a support surface with the desired item or items (sponges or storage device) being positioned on top for use. In still other embodiments, all or some of the sponges or towels may be may be stored within the compartments (e.g. one or more sponges within each compartment) of the device 150 so that do not spill out of the container 152 when removing the contents of the kit 146. The sponges or towels may then be removed from the compartments of the device or system 150 for use.

Figure 12:
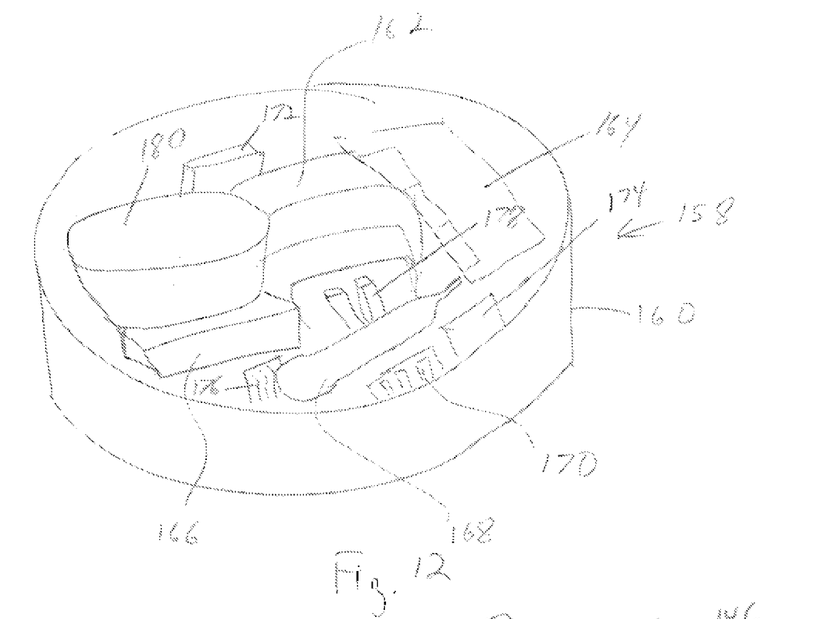
FIG. 12 is a perspective view of a procedural kit containing various items, including sponges and a storage system for surgical sponges, towels and other medical waste materials.

FIG. 12 shows another kit 158, which may be a procedural kit that is configured for use with a particular surgical procedure. The kit 158 may include a container 160, which may be a basin that may also be used for the procedure. The kit 158 includes various items, including sponges or towels 162, which may be the same or similar to the sponges or towels 148 previously described. The kit 158 also includes at least one storage device or system 164 for holding sponges or towels, which may be any of those that have been previously described herein. The device(s) 164 may be provided in a folded configuration. In certain embodiments, the number of compartments of the device or devices 164 may corresponding to the number of sponges or towels 162 contained in the kit 158. Other items provided in the kit may include, but are not limited to, a surgical instrument holder 166 (such as described in U.S. Pat. No. 6,827,212), a bulb syringe 168, suction tips 170, a needle counter box 172, disposable light handle covers 174, suture materials 176, skin stapler 178, a small basin or container 180, surgical masks and/or face shields (such as described in U.S. Pat. No. 7,540,039), surgical gloves, etc. The contents may be tailored to the particular procedure for which it is to be used. The container 160 or container opening may be wrapped or covered with paper or plastic wrap, film or other sheet material. The entire kit 158 with its components may be sterilized together or the components of the kit may be sterilized separately using known sterilization techniques. In certain embodiments, all or some of the sponges or towels of the kit 158 may be may be initially stored within the compartments of the device or system 164. The sponges or towels may then be removed from the compartments of the device or system 164 for use.

In use, the kit 158 is opened and the contents are used as needed, with the used sponges being stored and counted using the device or system 164 as has been described.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A storage device for storing used surgical towels, sponges or other medical waste materials, the storage device comprising:

a rear panel having an upper portion and a lower portion formed from a liquid impervious, polymeric flexible sheet material, the upper portion of the rear panel having a coupling mechanism for coupling the device to a sterile structure of a surgical room, the rear panel having a weakened partition area for separating the lower portion from the upper portion; and a compartment assembly formed by two or more flexible compartments formed from a liquid impervious, polymeric material provided on the lower portion of the rear panel, each compartment having an upper opening for introducing materials into the compartment, each compartment having a forward wall that is at least partially transparent so that the contents of the compartment are observable;

wherein all components of the storage device are sterile for use in a sterile environment;

wherein the coupling mechanism constitutes a layer of adhesive provided on the rearward surface of the upper portion of the rear panel; and the storage device is prepackaged with a mayo stand cover, wherein the storage device is adapted to be fixed to the mayo stand cover by the adhesive layer, and the lower portion is adapted to be removed from the mayo stand cover by separation at the weakened partition area.

2. The device of claim 1, wherein:

the device has at least one of the following (a)-(l):

(a) the compartment assembly has at least five (5) compartments;

(b) the compartments are gusseted to allow expansion of the compartments;

(c) indicia are provided on the device that includes at least one of compartment numbers, designated entry fields for entering of information on the device, measurement markings and a hazardous material indicator;

(d) the compartments are provided with a compartment closure for selectively closing the compartments;

(e) at least a portion of the rear panel is colored with a different color from the forward wall of the compartments;

(f) at least one compartment has a releasable divider that divides the at least one compartment into two sub-compartments, the two sub-compartments being eliminated when the releasable divider is released;

(g) a pull tab is provided at an upper portion of least one compartment to facilitate opening of the at least one compartment;

(h) the compartment assembly has at least two vertically spaced rows of compartments;

(i) the lower portion of the rear panel is provided with carry openings to facilitate carrying of at least one of the device and compartment assembly;

(j) an RFID is provided with the device;

(k) the rear panel has opposite facing compartments that can each be selectively used; and (l) the compartment assembly has at least ten (10) compartments.

3. The device of claim 2, wherein:

the device has at least two of (a)-(l).

4. The device of claim 1, wherein:

there are at least two devices that are each coupled together at the upper portion of each device.

5. The storage device of claim 1, wherein:

one or more of the compartments has a releasable divider that extends along all or a substantial portion of the length of the compartment and divides the compartment into two or more sub-compartments.

6. A storage system for storing used surgical towels, sponges or other medical waste materials, the storage system comprising:
   at least two sterile storage devices that are coupled together by coupling the upper portions of the rear panels together, each storage device comprising:
      a rear panel having an upper portion and a lower portion formed from a layer of liquid impervious, polymeric flexible sheet material, having a weakened partition area between the upper portion and the lower portion for separating the lower portion from the upper portion; and
      a compartment assembly formed by two or more flexible compartments provided on the lower portion of the rear panel, each compartment being liquid impervious and having an upper opening for introducing materials into the compartment, each compartment having a forward wall that is at least partially transparent so that the contents of the compartment are observable; and wherein
   at least a portion of one of the at least two storage devices is releasable from the other to facilitate use of the other device
   wherein the lower portion has a plurality of holes to facilitate hanging at least a portion of the storage device on a hanging structure when released from the other at least one storage device; wherein
   the lower portion has a plurality of hand openings, which are positioned between the weakened partition area and the plurality of holes, for carrying at least a portion of the device once released from the other at least one storage device; and wherein
   at least one of the two storage devices has a coupling mechanism formed by a layer of adhesive for coupling the storage devices to one another and for coupling the storage system to a structure.

7. The storage system of claim 6, wherein:
the system is sterile and prepackaged and incorporated with a drape or mayo stand cover at a sterile position thereon.

8. The storage system of claim 6, wherein:
the rear panel of at least one device is coupled to or forms a portion of the wall of a trash bag.

9. The storage system of claim 6, wherein:
the system has at least one of the following (a)-(j):
(a) the compartment assembly has at least five (5) compartments;
(b) the compartments are gusseted to allow expansion of the compartments;
(c) indicia are provided on each device that includes at least one of compartment numbers, designated entry fields for entering of information on the device, measurement markings and a hazardous material indicator;
(d) the compartments are provided with a compartment closure for selectively closing the compartments;
(e) at least a portion of the rear panel of at least one device is colored with a different color from the forward wall of the compartment of said at least one device;
(f) at least one compartment has a releasable divider that divides the at least one compartment into two sub-compartments, the two sub-compartments being eliminated when the releasable divider is released;
(g) a pull tab is provided at an upper portion of least one compartment to facilitate opening of the at least one compartment;
(h) the compartment assembly of at least one device has at least two vertically spaced rows of compartments;
(i) an RFID is provided with each device; and
(j) the compartment assembly has at least ten (10) compartments.

10. The system of claim 9, wherein:
the device has at least two of (a)-(j).

11. The system of claim 6, wherein:
each device has at least three compartments arranged in a side-by side configuration.

12. The system of claim 6, wherein:
the compartments of each device are provided with a compartment closure for selectively closing the compartments.

13. The system of claim 6, wherein:
the system is incorporated into one of a sterile sponge kit, a sterile medical drape, a sterile mayo stand cover, a surgical procedure kit and a trash bag.

14. The storage system of claim 6, wherein:
one or more of the compartments has a releasable divider that extends along all or a substantial portion of the length of the compartment and divides the compartment into two or more sub-compartments.

15. A kit comprising:
a container sealed with a removable cover, the container having a plurality of sponges and at least one storage device therein, wherein the at least one storage device comprises:
   a rear panel having an upper portion and a lower portion formed from a layer of liquid impervious, polymeric flexible sheet material, having a weakened partition area between the upper portion and the lower portion for separating the lower portion from the upper portion; and
   a compartment assembly formed by two or more flexible compartments provided on the lower portion of the rear panel, each compartment being liquid impervious and having an upper opening for introducing material into the compartment, each compartment having a forward wall that is at least partially transparent so that the contents of the compartment are observable;
   wherein the lower portion has a plurality of holes to facilitate hanging at least a portion of the storage device on a hanging structure when released from the other portion of the at least one storage device; and
   wherein all components of the storage device are sterile for use in a sterile environment.

16. The kit of claim 15, wherein:
one or more of the compartments has a releasable divider that extends along all or a substantial portion of the length of the compartment and divides the compartment into two or more sub-compartments.

* * * * *